United States Patent [19]

Evans et al.

[11] Patent Number: 5,675,055
[45] Date of Patent: Oct. 7, 1997

[54] ACIDIFICATION/EXTRACTION TREATMENT OF WASTE CAUSTIC STREAM

[75] Inventors: Thomas I. Evans, Glenmoore; Bernard Cooker, Malvern; Rajendra S. Albal, West Chester, all of Pa.

[73] Assignee: ARCO Chemical Technology, L.P., Greenville, Del.

[21] Appl. No.: 539,209

[22] Filed: Oct. 4, 1995

[51] Int. Cl.$^6$ .................. C07C 7/17; C07C 7/00
[52] U.S. Cl. .................. 585/858; 585/865; 585/866; 585/867
[58] Field of Search .................. 585/858, 865, 585/866, 867

[56] References Cited

U.S. PATENT DOCUMENTS

| | | | |
|---|---|---|---|
| 4,066,706 | 1/1978 | Schmidt | 260/610 B |
| 4,315,896 | 2/1982 | Taylor et al. | 423/54 |
| 4,405,572 | 9/1983 | Moore et al. | 423/54 |
| 5,171,868 | 12/1992 | Albal et al. | 549/529 |
| 5,210,354 | 5/1993 | Dubner et al. | 585/469 |
| 5,276,235 | 1/1994 | Dubner | 585/469 |

Primary Examiner—Walter D. Griffin
Assistant Examiner—In Suk Bullock
Attorney, Agent, or Firm—William C. Long

[57] ABSTRACT

The waste organics containing caustic stream from a propylene oxide/styrene monomer process is preferably first concentrated by distillation and then contacted with strong acid such as sulfuric acid and an organic solvent, the admixture is phase separated and an aqueous sodium containing phase reduced in organics is separated from an organic solvent phase reduced in sodium.

6 Claims, 1 Drawing Sheet

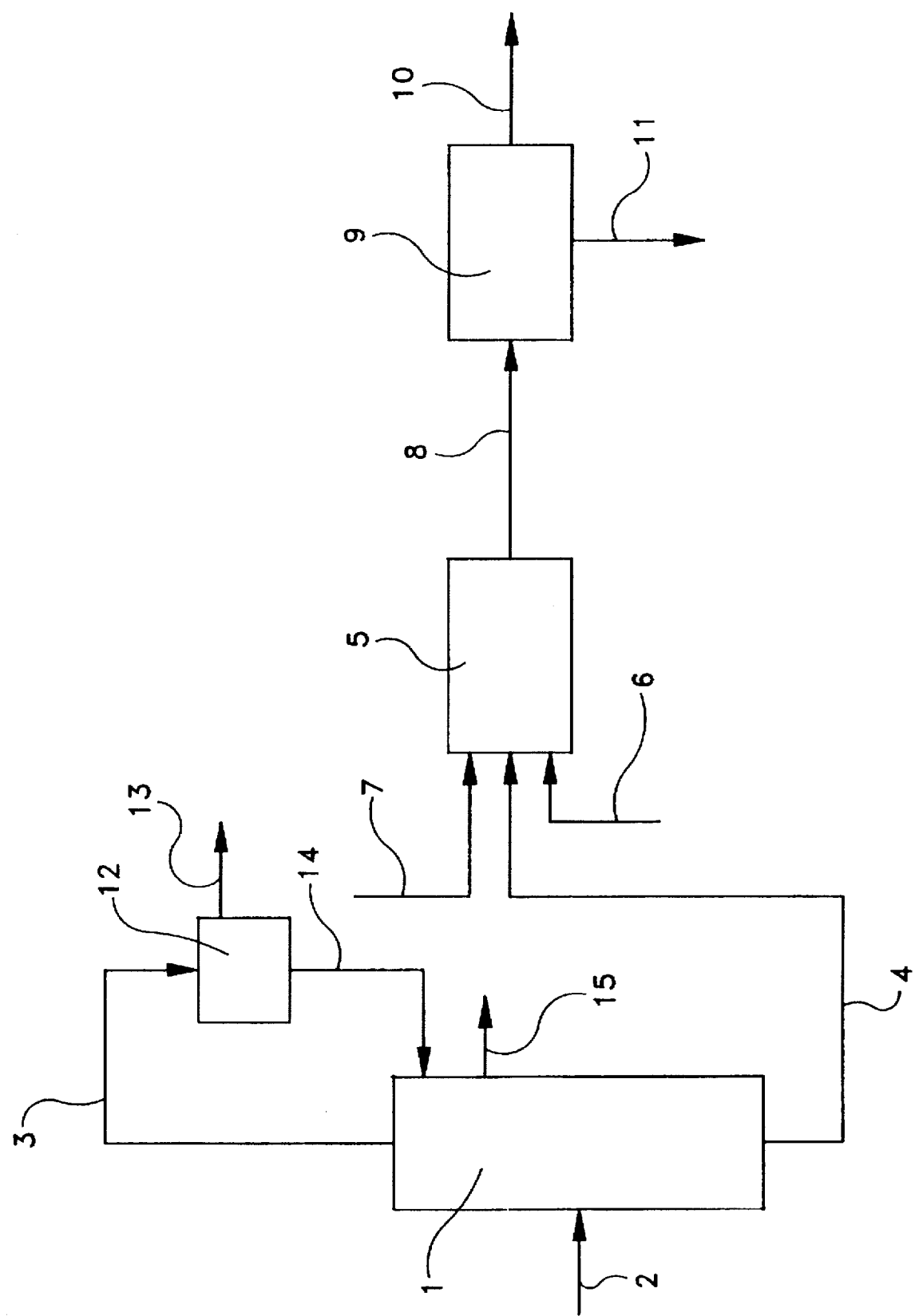

ACIDIFICATION/EXTRACTION TREATMENT OF WASTE CAUSTIC STREAM

FIELD OF THE INVENTION

The present invention relates to concentration and acidification/extraction treatment of spent organics containing caustic streams from propylene oxide and styrene monomer co-production.

DESCRIPTION OF THE PRIOR ART

An extremely successful process for the co-production of propylene oxide and styrene monomer involves the molecular oxygen oxidation of ethyl benzene to form ethyl benzene hydroperoxide, the catalytic reaction of the hydroperoxide with propylene to form propylene oxide and I-phenyl ethanol, and the dehydration of the I-phenyl ethanol to styrene monomer. The basic patent describing this process is U.S. Pat. No. 3,351,635.

In practice of the process, various distillation steps are employed in order to separate unreacted reagents as well as various product streams. Also one or more caustic wash steps are employed in order to remove contaminants such as phenols, molybdenum catalyst, and acids from various streams. Several purge streams result from these treatments including organic-containing aqueous spent caustic streams and a heavy organic residue stream containing high levels of sodium.

There are significant disposal problems associated with the heavy spent organic-containing caustic streams, especially in view of ever more rigorous environmental considerations. U.S. Pat. 5,210,354 provides a teaching of acidification and phase separation as a means of upgrading such heavy spent caustic streams with the recovery of useful materials therefrom.

Also, there are significant problems with burning the heavy organic residues containing high levels of sodium because of the resulting high ash which clogs and fouls boilers.

BRIEF DESCRIPTION OF THE INVENTION

In accordance with the present invention, the organic-containing spent caustic stream from propylene oxide/styrene monomer production, most preferably after distillation to separate water and to recover light organics, is treated with an aqueous strong acid, such as $H_2SO_4$, and with a higher boiling organic solvent such as the heavy organic residue produced in the propylene oxide/styrene monomer process in an acidification/extraction step. If predistillation is employed, the distilled salt-free water can be recycled as process water and the light organics can be burned as fuel. As a result of the acidification/extraction treatment, sodium present as sodium hydroxide and organic sodium salts is converted to the sodium salt of the acid e.g. sodium sulfate, which upon phase separation, is contained in the aqueous phase while organic components pass to the organic phase since the solubilities of these components are considerably less in acidic salt water than in basic caustic water. The organic solvent enhances the separation by homogenizing the organic phase and the fuel value of the heavy organic residue is improved as sodium is removed from it into the aqueous phase. The aqueous phase, substantially reduced in organics, can be much more readily disposed of by conventional means.

BRIEF DESCRIPTION OF THE DRAWING

The attached drawing illustrates in schematic form a practice of the invention.

DETAILED DESCRIPTION

In the propylene oxide/styrene monomer process, in a first reaction step, ethyl benzene is reacted with molecular oxygen at elevated temperature in accordance with known techniques to form ethyl benzene hydroperoxide; U.S. Pat. No. 4,066,706 provides a comprehensive description of the reaction. Then, ethyl benzene hydroperoxide is reacted with propylene to form propylene oxide and I-phenyl ethanol; U.S. Pat. No. 3,351,635 describes suitable conditions and catalysts for this epoxidation reaction.

The epoxidation reaction mixture is treated with aqueous caustic in order to separate molybdenum catalyst as well as organic components, such as acids and phenols. The treated epoxidate is distilled to separate the various components, including unreacted ethyl benzene, which can be recycled, preferably after caustic wash to remove acids as described in U.S. Pat. 3,439,001. The 1-phenyl ethanol formed during oxidation, epoxidation and acetophenone hydrogenation is dehydrated to product styrene as described in U.S. Pat. 3,351,635. This product can be caustic washed to separate phenols and acidic components.

As a result of the various caustic treatment procedures, a caustic waste stream is produced which contains molybdenum catalyst values, sodium hydroxide, organic sodium compounds, such as phenates and sodium acid salts, as well as various oxygenated organic materials. The disposal of the caustic waste stream has in the past posed considerable difficulties.

Generally the spent waste caustic stream has a composition by weight of 70 to 90% water, 1 to 4% NaOH, 3 to 10% Na organic salts, 2 to 10% total organic carbon, and 0.03 to 0.3% Mo compounds.

It is especially advantageous to distill the spent waste caustic stream, for example at 70° to about 110° C. and 100 mmHg to atmospheric pressure to separate water and lighter organics overhead from heavy residual. In this distillation a reflux ratio of 2/1 to 20/1 is generally employed with light organics taken as a net overhead for use as fuel and water taken as a side stream. The water can be recycled back to the process. Up to 60% or more of the spent waste caustic stream components can be distilled in this manner, producing a highly concentrated waste caustic stream and greatly reducing the volume in subsequent steps.

In accordance with the present invention, the concentrated waste caustic stream resulting from the above is treated with aqueous acid at least in amount sufficient to react with all of the contained sodium in the caustic stream. Sulfuric acid is the preferred acid since it reacts with the sodium values to form sodium sulfate which is relatively acceptable for purposes of disposal. Less preferred acids include hydrochloric acid, phosphoric acid and the like. A higher boiling organic solvent is also employed in the treatment of the waste caustic stream. Especially preferred is a highly aromatic residual fuel oil fraction obtained from the propylene oxide/styrene process, because it is inexpensive, readily available, is essentially immiscible with salt water, and its high aromatic content is effective in extracting comparable aromatic materials from the spent caustic stream. Alternatively, higher boiling hydrocarbon solvents can be used, illustratively hydrocarbons having 8 to 20 carbon atoms as well as organics such as bis-alpha methyl benzyl ether and propylene glycol oligomers. The acidification/extraction treatment greatly reduces the sodium content of the residual fuel oil used. This increases the fuel value of the residual fuel oil while it adds additional salt to the aqueous phase thus dispersing additional organics out of the aqueous phase into the organic phase.

The acidification/extraction treatment is carried out at 15 to 90 degrees C, preferably 25 to 45 degrees C and preferably at atmospheric pressure although this is not critical. The caustic stream, acid and organic solvent are thoroughly admixed and allowed to settle into distinct immiscible phases. The acid is used in at least the stoichiometric amount necessary to react with all the contained sodium values and to attain an acidic pH of the mix, preferably a pH value of 1 to 3. This serves to break the sodium-organic salts into the respective organic acids which can then transfer to the organic phase. Generally the organic solvent is employed in at least a volume equal to 8% of the spent caustic stream. Preferably 8 to 35 volumes of solvent per 100 volumes of the spent caustic stream is used.

Through practice of the invention, organics contained in the waste caustic stream are recovered in the organic phase and can be used as fuel in boiler systems. The aqueous stream is greatly reduced in organics and is amenable to further organics-reducing treatments. The organic product is increased in size and its sodium content is greatly reduced.

Referring to the drawing, a combined aqueous waste caustic stream resulting from caustic treatment of the propylene/ethylbenzene hydroperoxide epoxidation reaction product mixture and from caustic treatment of styrene formed by 1-phenyl ethanol dehydration is fed to distillation column 1 via line 2. In column 1, a light organics and water stream is distilled overhead and removed via line 3. The vapor stream is condensed (not shown) and the resulting liquid is phase separated in separator 12. The supernatant organic phase is recovered via line 13 and comprises a valuable product; organics contained therein comprise methanol, ethyl benzene, styrene, 1-phenyl ethanol, acetophenane and the like.

The aqueous phase from separator 12 is returned to column 1 via line 14 as a reflux stream. A water stream is removed via line 15 as a sidestream and is of a quality suitable for recycle or biotreatment or the like. It is generally preferred to separate 45 to 60% by weight of the feed via lines 13 and 15; further removal may result in excessively viscous bottoms.

Bottoms from Column 1 comprises a stream concentrated in sodium and molybdenum values, and this stream passes via line 4 to mixing zone 5 wherein it is throughly admixed with aqueous acid, preferably concentrated sulfuric acid, introduced via line 6 and with an organic solvent introduced via line 7. The organic solvent is immiscible with water and capable of extracting organics such as acids and phenols from the aqueous acid salt phase.

The mixture from mixing zone 5 passes via line 8 to decantation zone 9 wherein two immiscible phases separate. The upper organic phase comprised of solvent together with oxygenated organics from the waste caustic stream such as acids, phenols, ketones, and the like and a lower aqueous phase containing sodium and molybdenum values and greatly reduced in organics.

The supernatant organic phase is separated via line 10 and can be used as boiler fuel. The heavy aqueous phase is removed via line 11 and sent on to further organic-reducing treatments.

The combined acidification/extraction treatment of the invention substantially improves resolution of the waste caustic as compared to acidification alone, and greatly facilitates further treatment and disposal procedures such as biotreatment or wet air oxidation.

EXAMPLE

The following example, which is described with reference to the accompanying drawing, illustrates the invention.

A waste caustic stream from a propylene oxide/styrene monomer process is fed at the rate of 60,000 lbs/hr to distillation column 1. The waste stream is a combined stream from the caustic treatment of the epoxidate and of the styrene formed by dehydration and has the following composition by weight: 89% water, 1.6% sodium, 0.035% Mo, 5% total organic carbon, 1.4% propylene glycol, 0.8% phenols, and 0.2% 1-phenyl ethanol, 1.4% sodium benzoate, and about 1.0% other sodium organic salts.

Column 1 has 7 theoretical stages and is operated at an overhead pressure of 760 mmHg and 100° C. Vapors are removed via line 3 at the rate of 3840 lbs/hr and comprise 91wt. % water and 9wt. % organic materials. The overhead is cooled to 20° C. to condense the components and is passed to phase separator 12. An organic phase is recovered via line 13 at the rate of 270 lbs/hr. comprised by weight of 0.45% ethylbenzene, 4.5% methanol, 83% 1-phenyl ethanol, 5.4% acetophenone, 2.2% allyl alcohol, and about 5% other organics. The aqueous phase from separator 12 is returned via line 14 to column 1 as reflux at the rate of 3570 lbs./hr.

A side stream comprised by weight of 99.1% water is removed via line 15 at the rate of 38,130 lbs/hr. and is suitable for further biotreatment. This sidestream is removed after the third theoretical tray location from the top.

Bottoms at the rate of 21600 lbs/hr., concentrated in Na and Mo, is removed at 110° C. and 14.9 psia via line 4 and passes to mixing zone 5 wherein it is admixed with 2300 lbs/hr 96% $H_2SO_4$ in water and with 6000 lbs/hr of residual fuel oil solvent which is mainly comprised of bis-alpha methyl benzyl ether and propylene glycol oligomers and which has the following composition and characteristics:

Basicity 0.42 meg/g, sulfur <5 ppm, water 0.53 wt %, spec. gravity 1.08 @25° C., flash point 250° F., viscosity 1000 cp @25° C., ash 7.1 wt %, Na 0.95 wt %, Mo 100 ppm, elemental composition by weight of 73% carbon, 8% hydrogen and 19% oxygen.

The resulting admixture is passed to decantation zone and separated into two immiscible phases. The upper organic solvent phase is removed via line 10 at the rate of 9700 lbs/hr and has the following composition and characteristics: Acidity 1.5 meg/g, sulfur 100 ppm, water 4.5 wt%, flash point >250° F., specific gravity 1.08 @25° C., viscosity 153 cp @25° C., ash <0.5%, sodium 90 ppm, Mo 190 ppm. The mixture, improved particularly by lower ash and sodium content, can be used directly as fuel.

The lower aqueous phase is removed via line 11 at the rate of 20200 lbs/hr and has the following composition by weight: 77% water, 4.6% Na, 0.092% Mo, 4.5% total organic carbon, 4.5% propylene glycol, 0.22% phenols, 0.07% 1-phenyl ethanol and 0.12% benzoic acid. This is a total reduction in organics of over 60% with the primary organics removed being benzoic acid, phenols, and 1-phenyl ethanol. The remaining organics, primarily propylene glycol, are amenable to subsequent treatment. This substantially reduces the organic load put on downstream treatments, such as biotreatment or wet air oxidation.

The above demonstrates the improved separation achieved through practice of the invention.

We claim:

1. In a process for the treatment of a waste caustic stream from the propylene oxide and styrene monomer process, the improvement which comprises admixing the said waste caustic stream with aqueous acid and water-immiscible organic solvent, phase separating the resulting admixture into an aqueous sodium containing phase and an organic phase having a reduced sodium content, and separately recovering the phases.

2. The process of claim 1 wherein the said aqueous acid is aqueous sulfuric acid.

3. The process for the treatment of the waste caustic stream from the propylene oxide and styrene monomer process which comprises distilling the waste stream to separate water and light organics from a concentrated aqueous waste caustic bottoms stream, admixing the concentrated bottoms stream with aqueous acid and water-immisicible organic solvent, phase separating the resulting admixture into an aqueous sodium containing phase and an organic phase having a reduced sodium content and separately recovering the phases.

4. The process of claim 3 wherein at least 50% of the waste caustic stream is separated by distillation from the concentrated aqueous bottoms stream.

5. The process of claim 3 wherein the acid is aqueous sulfuric acid.

6. The process of claim 1 wherein the organic solvent is a residual fuel oil from the propylene oxide and styrene monomer process mainly comprised of bis-alpha methyl benzyl ether and propylene glycol oligomers.

* * * * *